United States Patent
Matsuda (10) Patent No.: US 8,074,305 B2
(45) Date of Patent: Dec. 13, 2011

(54) BUBBLING BATH ADDITIVE AND BUBBLING BATH ADDITIVE CONTAINER

(75) Inventor: Toyohiro Matsuda, Kanazawa (JP)

(73) Assignee: Kabushiki Kaisha Health, Kanazawa-shi (JP)

( * ) Notice: Subject to any disclaimer, the term of this patent is extended or adjusted under 35 U.S.C. 154(b) by 1279 days.

(21) Appl. No.: 11/597,530

(22) PCT Filed: May 26, 2005

(86) PCT No.: PCT/JP2005/009681
§ 371 (c)(1),
(2), (4) Date: Apr. 12, 2007

(87) PCT Pub. No.: WO2005/115329
PCT Pub. Date: Dec. 8, 2005

(65) Prior Publication Data
US 2008/0313800 A1    Dec. 25, 2008

(30) Foreign Application Priority Data

May 27, 2004   (JP) ................................ 2004-157346
Jul. 7, 2004    (JP) ................................ 2004-200874

(51) Int. Cl.
*A47K 3/00* (2006.01)
(52) U.S. Cl. ................. 4/559; 4/514; 4/661; 4/DIG. 10; 510/130; 424/466; 446/163
(58) Field of Classification Search ............ 4/514, 559, 4/661, DIG. 10; 510/130, 135, 141, 145; 424/466; 446/153, 160, 163, 211
See application file for complete search history.

(56) References Cited

U.S. PATENT DOCUMENTS

| | | | | | |
|---|---|---|---|---|---|
| 4,292,758 | A | * | 10/1981 | Kuna et al. | 446/163 |
| 5,198,144 | A | * | 3/1993 | Ichii et al. | 510/130 |
| 5,566,491 | A | * | 10/1996 | Phillips | 446/163 |
| 5,955,057 | A | * | 9/1999 | Maunder et al. | 424/466 |
| 6,121,215 | A | | 9/2000 | Rau | 510/130 |
| 2003/0194434 | A1 | | 10/2003 | Watanabe et al. | 424/466 |

FOREIGN PATENT DOCUMENTS

| | | |
|---|---|---|
| JP | 61-008099 U | 1/1986 |
| JP | 63-109198 U | 7/1988 |
| JP | 64-043992 U | 3/1989 |
| JP | 09-002942 A | 1/1997 |
| JP | 11-207045 A | 8/1999 |
| JP | 2003-103064 A | 4/2003 |
| JP | 2003-261188 A | 9/2003 |
| WO | 01/52820 A1 | 7/2001 |

* cited by examiner

*Primary Examiner* — Steven J Ganey
(74) *Attorney, Agent, or Firm* — Kubovcik & Kubovcik (57) ABSTRACT

A bubbling bath additive 42 made of a surfactant 46 and a bubbling agent 44, and a housing member 12 for housing the bubbling bath additive 42 are provided. A floating part 22, 34 that is situated above the housing member 12 and floats on the water surface, and an ejection port 33 that is provided above the waterline of the floating part 22, 34 and through which bubbles formed by the bubbling bath additive 42 are ejected outward from inside, are provided. A suction port 14 through which water flows inward from outside is provided near a lower end part of the housing member 12.

9 Claims, 6 Drawing Sheets

BUBBLING BATH ADDITIVE AND BUBBLING BATH ADDITIVE CONTAINER

This application is a 371 of international application PCT/JP2005/009681, which claims priority based on Japanese patent application Nos. 2004-157346 and 2004-200874 filed May 27 and Jul. 7, 2004, respectively, which are incorporated herein by reference.

TECHNICAL FIELD

This invention relates to a bubbling bath additive that is to be put and caused to bubble into a bathtub at the time of bathing, and a bubbling bath additive container.

BACKGROUND ART

Conventionally, there have been various types of bath additives to be put into a bathtub, for example, liquid, powder, solid and the like. Solid bath additives include those that are put into a container like a toy floating in hot water and are dissolved on the water surface, as well as those that are put directly into hot water and then sunk and dissolved.

Such containers housing a solid bath additive and floating on water surface include a toy of Patent Reference 1 and a bath additive toy of Patent Reference 2. These containers have a buoyant unit and a hollow part forming unit attached below the buoyant unit and adapted for putting a carbon dioxide bubbling bath additive therein, and a permeating hole for ejecting bubbles is provided at one position in the hollow part forming unit. The way to use these containers is to put a carbon dioxide bubbling bath additive into the hollow part forming unit and put the container into a bathtub. Then, the container is submerged in bath water and the carbon dioxide bubbling bath additive starts dissolving. The active ingredients are eluted and carbon dioxide gas is generated. Then, the carbon dioxide gas pressure is applied within the hollow part forming unit and the hot water in the hollow part forming unit is ejected from the permeating hole. The toy moves into the opposite direction to the permeating hole.

As a container that does not move in one direction but rotates substantially at a constant position, there is a float for housing a bath additive of Patent Reference 3. This float has a float body having a lid unit, and a bubbling bath additive arranging part is provided within the float body. A pair of through-holes is formed at parts substantially facing each other of the float body. These through-holes are provided horizontally to the wall of the toy body with an inclination in the same direction. The way to use this container is to put a bubbling bath additive into the float body and sink it into a bathtub. Then, the active ingredients are eluted and carbon dioxide gas is generated. The hot water in the toy body is ejected obliquely from the through-holes, and its repulsive force rotates the float body. After the lapse of a predetermined time, the water surface in the float body is lowered and the gas pressure in the float body temporarily escapes outward. The above discharge stops. After that, when the container is filled with gas with the lapse of time, discharge starts again and the float body rotates.

Patent Reference 1: JP-A-11-207045
Patent Reference 2: JP-A-2003-103064
Patent Reference 3: Japanese Utility Model Registration No. 2564374

DISCLOSURE OF THE INVENTION

Problems that the Invention is to Solve

The conventional containers to put a solid bubbling bath additive therein are toys for children. These containers were to move in one direction or rotate intermittently. However, they did not have the function of evenly spreading the eluted ingredients of the bath additive on the water surface. Also, the bath additives used for these simply contained hot spring elements, aromatic elements, coloring elements or carbon dioxide elements that promote blood circulation, and did not float minute bubbles on the surface of bath water. Meanwhile, with bath additives containing soap elements like bubble bath, it was difficult to evenly spread fine bubbles on the water surface in the bathtub.

In view of the foregoing status of the art, it is an object of this invention to provide a bubbling bath additive and a bubbling bath additive container that enable easy formation of even bubbles and spreading on the surface of bath water.

Means for Solving the Problems

This invention provides a bubbling bath additive made by forming powder particles of a bubbling agent that generates carbon dioxide gas and powder particles of a surfactant element into a disc shape or other predetermined shapes. A part made by forming the bubbling agent powder and a part made by adding a bath additive element to soap element powder that is the surfactant may be separately formed. Moreover, a bathtub detergent may be used as the surfactant and may be used as for cleaning the bathtub after bathing.

This invention also provides a bubbling bath additive container having a housing member that houses a bubbling bath additive made of a surfactant and a bubbling agent, a floating part that is situated above this housing member and floats on a water surface, an ejection port that is provided above a waterline of the floating part and through which bubbles formed by the bubbling bath additive are ejected outward from inside, and a suction port that is formed near a lower end part of the housing member and through which water flows inward from outside.

The floating part is formed substantially in a circle, and the ejection port is provided concentrically with an upper surface of the floating part. A plurality of the ejection ports is provided at substantially equal intervals along a circumferential direction of the floating part. Also, on the upper surface of the floating part, a recessed part provided radially toward a circumferential edge part is arranged next to the ejection port.

The bubbling bath additive is situated above the suction port of the housing member. The housing member is provided with an inner bottom part having a permeating hole between the suction port and the floating part, and the bubbling bath additive is situated in the inner bottom part.

This invention also provides a bath additive container having a hollow body with a part thereof situated below a water surface. The body has a lower body part that is situated below the water surface and houses therein a bubbling bath additive including a surfactant and a bubbling agent, a suction port that is provided in the lower body part and through which water flows inward from outside, an upper body part that is situated above the water surface and forms a bubble housing space with its inside filled with bubbles formed by the bubbling bath additive and the surfactant, and an ejection port that is provided above and near the water surface and through which the bubbles filling the bubble housing space are ejected outward from inside.

This invention also provides a bath additive container having a hollow body floating on a water surface with a part thereof situated below a waterline. The body has a lower body part that is situated below the water surface and houses therein a bubbling bath additive including a surfactant and a bubbling agent, a suction port that is provided in the lower body part and through which water flows inward from outside, an upper body part that is situated above the water surface, is mounted to the lower body part and forms a bubble housing space with its inside filled with bubbles formed by the bubbling bath additive, and an ejection port that is provided above and near the waterline and through which the bubbles filling the bubble housing space are ejected outward from inside.

The body is provided with a floating member that adjusts the position of the body relative to the water surface, and it is adjusted so that the bubble housing space is situated above the water surface. The body is provided with a weight that adjusts the position of the body relative to the water surface, and it is adjusted that the bubbling bath additive is situated below the water surface. The suction port is provided in a bottom part of the body, and inside the suction port, a holding member that holds the bath additive is fixed to the lower body part. The holding member is shaped to be situated to cover the suction port, and a permeating hole through which water flows is formed in the holding member.

Advantage of the Invention

In the bubbling bath additive container according to this invention, its simple structure causes sufficient bubbling by the surfactant and the bubbling agent element, and the entire water surface in the bathtub can be filled with fine bubbles. Thus, when entering the bathtub, one can conformably bath, feeling the touch of bubbles.

Also, the bubbling bath additive according to this invention enables easy floating of fine bubbles on the water surface by using the bubbling agent and the surfactant, and it can be readily used as a bath additive and bathtub detergent.

DESCRIPTION OF REFERENCE NUMERALS AND SIGNS 10 bubbling bath additive container
12 housing member
14 suction port
18 lower case
20 cylindrical part
22 lower floating part
28 upper case
30 lid part
32 supporting part
33 ejection port
34 upper floating part
36 engagement groove
40 recessed part
42 bubbling bath additive
44 bubbling agent
46 surfactant

BEST MODE FOR CARRYING OUT THE INVENTION

Hereinafter, embodiments of this invention will be described with reference to the drawings. FIGS. 1 to 4 show a first embodiment of this invention. A bubbling bath additive container 10 of this embodiment is provided with a substantially conical housing member 12 in which a bubbling bath additive 42, later below, is to be put. The housing member 12 is made of a flexible synthetic resin or the like, and for example, four suction ports 14 as permeating holes are formed at equal intervals in the circumferential direction near a peak part 12a. Within the housing member 12, a shape holding ring 16 is fitted at a part slightly farther from the peak part 12a than the suction ports 14, perpendicularly to the center axis of the housing member 12, and thus holds the shape of the housing member 12. The shape holding ring 16 may be attached appropriately.

Figure 1:
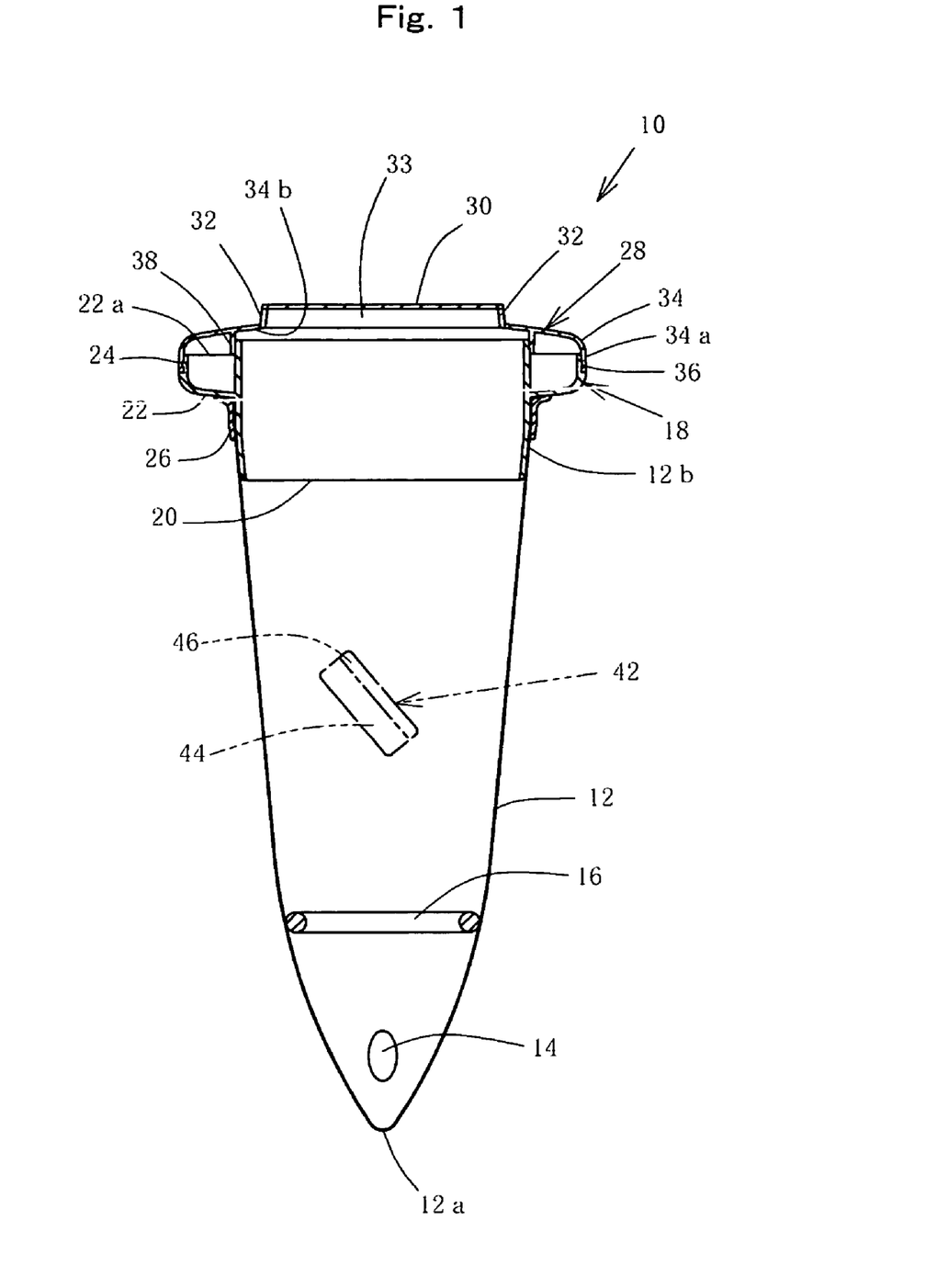
FIG. 1 is a longitudinal sectional view of a bubbling bath additive container according to a first embodiment of this invention.

A lower case 18 made of a hard synthetic resin is mounted on an aperture part 12b opposite to the peak part 12a of the housing member 12. The lower case 18 is provided with a cylindrical part 20 that is inserted to the inside of the aperture part 12b of the housing member 12. On the outer surface of the cylindrical part 20, a lower floating part 22 expanding outward substantially at right angles to the cylindrical part 20 from a halfway part of the cylindrical part 20 is integrally provided. A circumferential edge part 22a of the lower floating part 20 is curved upward in a saucer-shape. An engagement protrusion 24 that retains an upper floating part of an upper case 28, described below, is formed around the outer circumferential surface of the circumferential edge part 22a of the lower floating part 22.

The aperture part 12b of the housing member 12 is situated near the boundary between the cylindrical part 20 of the lower case 18 and the lower floating part 22, and a holding ring 26 that holds the housing member 12 against the cylindrical part 20 of the lower case 18 is fitted with the outer surface of the aperture part 12b of the housing member 12. The cross-sectional shape of the holding ring 26 is an L-shape that tightly contacts the part near the boundary between the cylindrical part 20 and the lower floating part 22.

A disc-shaped upper case 28 that covers the top side of the lower case 18 is attached to the lower case 18. The upper case 28 is made of a hard synthetic resin like the lower case 18. A central part of the upper case 28 is formed as a disc-shaped lid part 30. On the lower side of the circumferential edge part of the lid part 30, four supporting parts 32 are formed downward at equal intervals in the circumferential direction. At the lower ends of the respective supporting parts 32, a doughnut-shaped upper floating part 34 is integrally provided. A space surrounded by a pair of supporting parts 32, the lid part 30 and the upper floating part 34 is an ejection port 33. An outer circumferential edge part 34a of the upper floating part 34 is curved downward, and an engagement groove 36 that retains the engagement protrusion 24 of the lower floating part 22 of the lower case 18 is provided around the inner surface of the curve. On the lower side of the upper floating part 34 between the outer circumferential edge part 34*a* and an inner circumferential edge part 34*b*, a cylindrical fixing part 38 fitted with the outer surface of the cylindrical part 20 of the lower case 18 is provided.

Figures 2A, 2B, 2C:
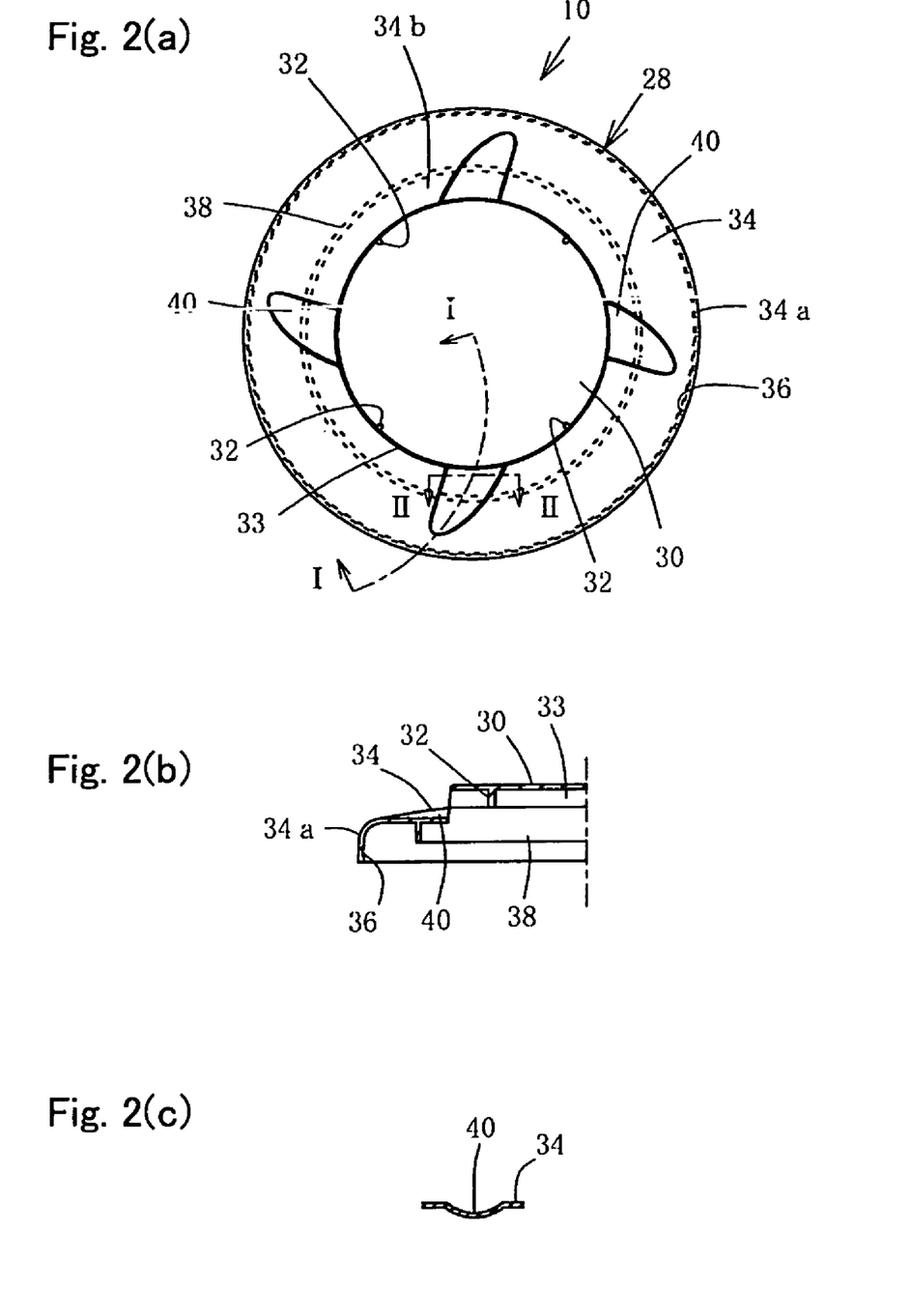
FIG. 2 is a top view (A) of an upper case of the bubbling bath additive container according to the first embodiment of this invention, a I-I sectional view (B), and a II-II sectional view (C) of a recessed part.
Figure 3:
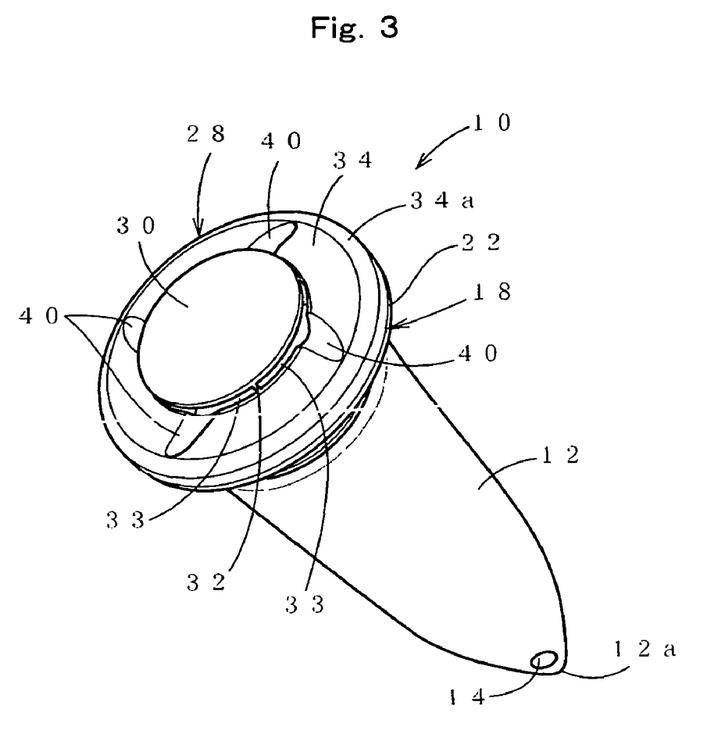
FIG. 3 is a perspective view of the bubbling bath additive container according to the first embodiment of this invention, as viewed from the upper case side.
Figure 4:
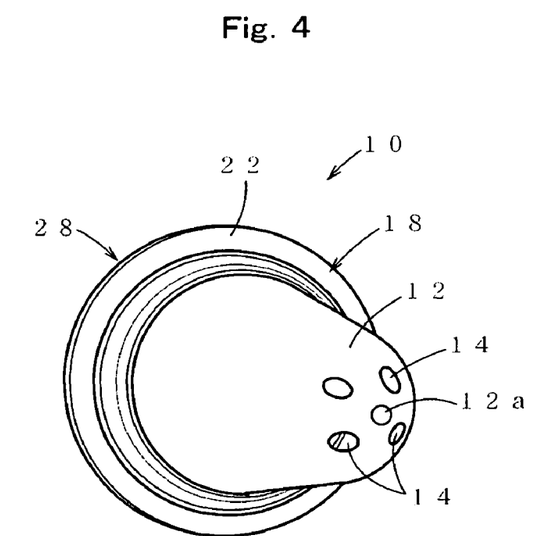
FIG. 4 is a perspective view of the bubbling bath additive container according to the first embodiment of this invention, as viewed from the housing member side.

In the upper floating part 34, a recessed part 40 is provided at the intermediate position of a pair of supporting parts 32, substantially radially from the inner circumferential edge part 34*b* of the upper floating part 34, as shown in FIG. 2. The distal end of the recessed part 40 toward the outer circumferential edge part 34*a* is curved in a predetermined direction with respect to the radial direction. Here, in FIG. 2, the outer distal end of the recessed part 40 is curved clockwise. The recessed part 40 has its width narrowed toward the outer distal end.

Within the housing member 12 attached to the lower case 18, a solid bubbling bath additive 42 containing bath additive ingredients for moisturizing and promoting blood circulation is put. The bubbling bath additive 42 is made by forming powder particles of a bubbling agent 44 that generates carbon dioxide gas and powder particles of a surfactant 46 such as soap element, into a predetermined shape, and has a two-layer or two-unit structure of these. The layer of the bubbling agent 44 and the layer of the surfactant 46 containing the other bath additive ingredients are provided as discs with the same diameter. The surfactant 46 is formed to be thinner than the bubbling agent 44. As the bath additive ingredients to be contained in the bubbling bath additive 42, various hot spring elements and the like can be selected appropriately.

The elements of the layer of the bubbling agent 44 are, for example, sodium carbonate at 50%, succinic acid 42%, polyvinyl pyrrolidone or malic acid 1%, lubricant such as polyethylene glycol 5%, powder detergent 2% and the like. The layer of the surfactant 46 may include sodium bicarbonate at 18%, sodium carbonate 25%, succinic acid 25%, lubricant 20%, powder detergent 12% and the like. These elements and the configuration of the layer can be properly changed.

Next, the way of using the bubbling bath additive container 10 of this embodiment will be described. First, the upper case 28 is opened from the lower case 18, and the bubbling bath additive 42 is put into the housing member 12. The engagement protrusion 24 of the lower case 18 is elastically deformed and inserted into the engagement groove 36 of the upper case 28, and thus retained. In this state, the bubbling bath additive container 10 together with the bubbling bath additive 42 is put into bath water in a bathtub. In the bubbling bath additive container 10, a floating part surrounded by the upper floating part 34 of the upper case and the lower floating part 22 of the lower case 18 is formed and air is enclosed in that space. The bubbling bath additive container 10 floats on the water surface of the bath water, and the housing member 12 is situated below the water surface of the bath water. Also, in this state, the ejection port 33 is situated above the water line.

Bath water enters from the suction ports 14 of the housing member 12 and dissolves the bubbling agent 44 and the surfactant 46 of the bubbling bath additive 42. The generated carbon dioxide strikes the dissolved surfactant 46, which is then stirred and bubbles. The bubbles formed by this surfactant 46 rises and ejected outward from the ejection port 33 between the supporting parts 32 of the upper case 28. In this case, the inner space of the cylindrical part 20 of the lower case 18 that is within the ring shape of the upper floating part 34 and the lower floating part 22 is a space where the bubbles formed by the surfactant and air bubbles are gathered, and the bubbles can be ejected continuously from the ejection port 33. The ejected bubbles are ejected in a predetermined direction along the recessed part 40. Then, the repulsive force of the ejected bubbles causes the bubbling bath additive container 10 to rotate in a predetermined direction. The bubbles automatically spread on the surface of the bath water and fill the bathtub.

With the bubbling bath additive container 10 of this embodiment, bubbles of the surfactant 46 can be easily formed and fill the bathtub. When bathing, one can feel the touch of bubbles and comfortably wash the body. The bubbling bath additive 42 satisfactorily bubbles since it is divided into the two layers of the bubbling agent 44 and the surfactant 46. The housing member 12 is prevented from crushing by the shape holding ring 16, and bubbling and flow of bubbles and water are made smoothly without any trouble.

Figure 5:
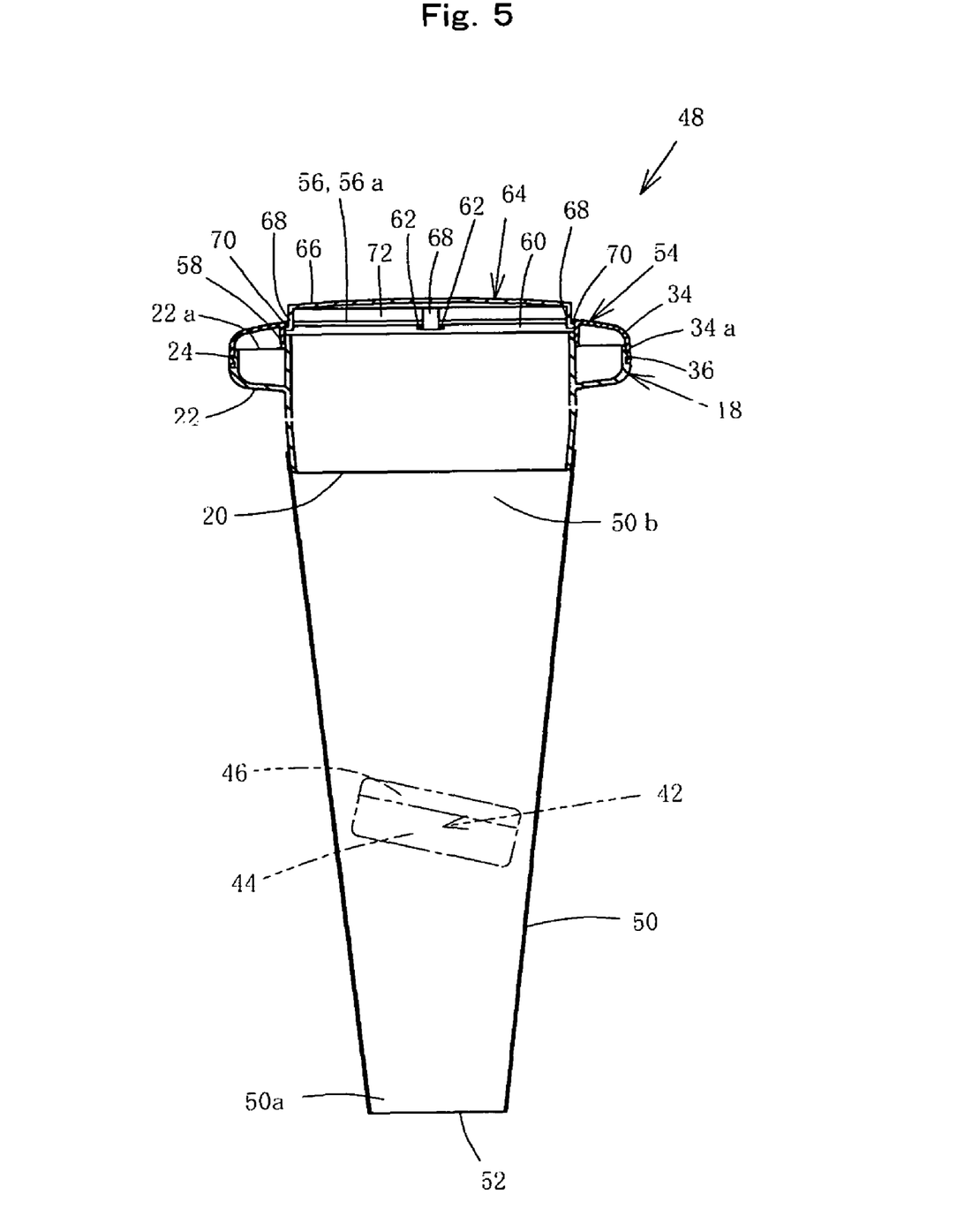
FIG. 5 is a longitudinal sectional view of a bubbling bath additive container according to a second embodiment of this invention.

Next, a second embodiment of this invention will be described with reference to FIG. 5. Here, the same members as in the above embodiment are denoted by the same numerals and will not be described further in detail. A bubbling bath additive container 48 of this embodiment is provided with a bag-like housing member 50, which is a housing member to put the bubbling bath additive 42 therein. The housing member 50 is made of a cylindrical unwoven fabric and formed in a conical shape with one end part 50*a* of the housing member 50 being narrowed in width than the other end part 50*b*. The one end part 50*a* of the housing member 50 is open, forming a suction port 52. The other end part 50*b* of the housing member 50 is attached with an adhesive or the like near a lower end part of the outer surface of the cylindrical part 20 of the lower case 18.

In the lower case 18, the lower floating part 22 is integrally provided from a halfway part on outer surface of the cylindrical part 20. The engagement protrusion 24 is formed around the outer circumferential surface of the circumferential edge part 22*a* of the lower floating part 22, and a ring-shaped upper case 54 covering the top side of the lower case 18 is mounted. A center part of the upper case 54 is formed as an aperture part 56 continuing to the cylindrical part 20 of the lower case 18. On a slightly outer side of a circumferential edge part 56*a* of the aperture part 56, a cylindrical fixing part 58 to be fitted with the outer surface of the cylindrical part 20 of the lower case 18 is provided. The surrounding part of the aperture part 56 is the doughnut-shaped upper floating part 34, and the outer circumferential edge part 34*a* of the upper floating part 34 is curved downward. The engagement groove 36 that retains the engagement protrusion 24 of the lower floating part 22 of the lower case 18 is provided around the inner surface of the curve.

In the upper floating part 34, the recessed part 40 is provided substantially radially from the circumferential edge part 56*a* of the aperture part 56. The recessed part 40 is provided at four positions that quadrisect the circumferential edge part 56*a* of the aperture part 56. On an inner surface 60 of the cylindrical fixing part 58, a pair of guide protrusions 62 is formed and arrayed along the circumferential edge part 56*a* of the aperture part 56, at an intermediate position of a pair of recessed parts 40 near the circumferential edge part 56*a* of the aperture part 56.

A lid member 64 is mounted to be attachable to and removable from the aperture part 56 of the upper case 54, and a disc part 66 having substantially the same size as the aperture part 56 and slightly curved upward is provided on the lid member 64. At four positions spaced at equal intervals on the circumferential edge part of the disc part 66, a supporting part 68 protruding downward from the disc part 66 is provided, and a retaining protrusion 70 protruding outward is provided at the lower end part of the supporting part 68. The width of the supporting part 68 is defined so that will be fitted with a small margin between a pair of guide protrusions 62 provided on the inner surface of the cylindrical fixing part 58. The retaining protrusion 70 of the supporting part 68 is fitted and attached into a groove part formed by being surrounded by the circumferential edge part 56a of the aperture part 56 of the upper case 54, the cylindrical fixing part 58 and the cylindrical part 20 of the lower case 18, as the supporting part 68 is elastically deformed. In this case, the space surrounded by a pair of supporting parts 68, the disc part 66 and the upper floating part 34 is an ejection port 72.

Next, the way of using the bubbling bath additive container 48 of this embodiment will be described. First, The upper case 54 is attached to the lower case 18, and the bubbling bath additive 42 is put into the housing member 50. The supporting part 68 of the lid member 64 is elastically deformed and inserted to the lower side of the circumferential edge part 56a of the aperture 56 of the upper case 54, and the lid member 64 is retained to the upper case 54. In this state, the bubbling bath additive container 48 together with the bubbling bath additive 42 is put into bath water in a bathtub.

Bath water enters from the suction port 52 of the housing member 50 and dissolves the bubbling agent 44 and the surfactant 46 of the bubbling bath additive 42. The generated carbon dioxide strikes and stirs the dissolved soap element and thus forms bubbles. These bubbles rise and are accumulated in the ejection port 72 between the upper case 54 and the lid member 64, and are then ejected outward from the ejection port 72. The ejected bubbles are ejected in a predetermined direction along the recessed part 40. The repulsive force of the ejected bubbles causes the bubbling bath additive container 48 to move or rotate in a predetermined direction. The bubbles automatically spread on the surface of the bath water and fill the bathtub.

The bubbling bath additive container 48 of this embodiment has the same effects as in the foregoing embodiment. Since the housing member 50 is made of an unwoven fabric, the cost is low and it is easy to process and handle.

Figure 6:
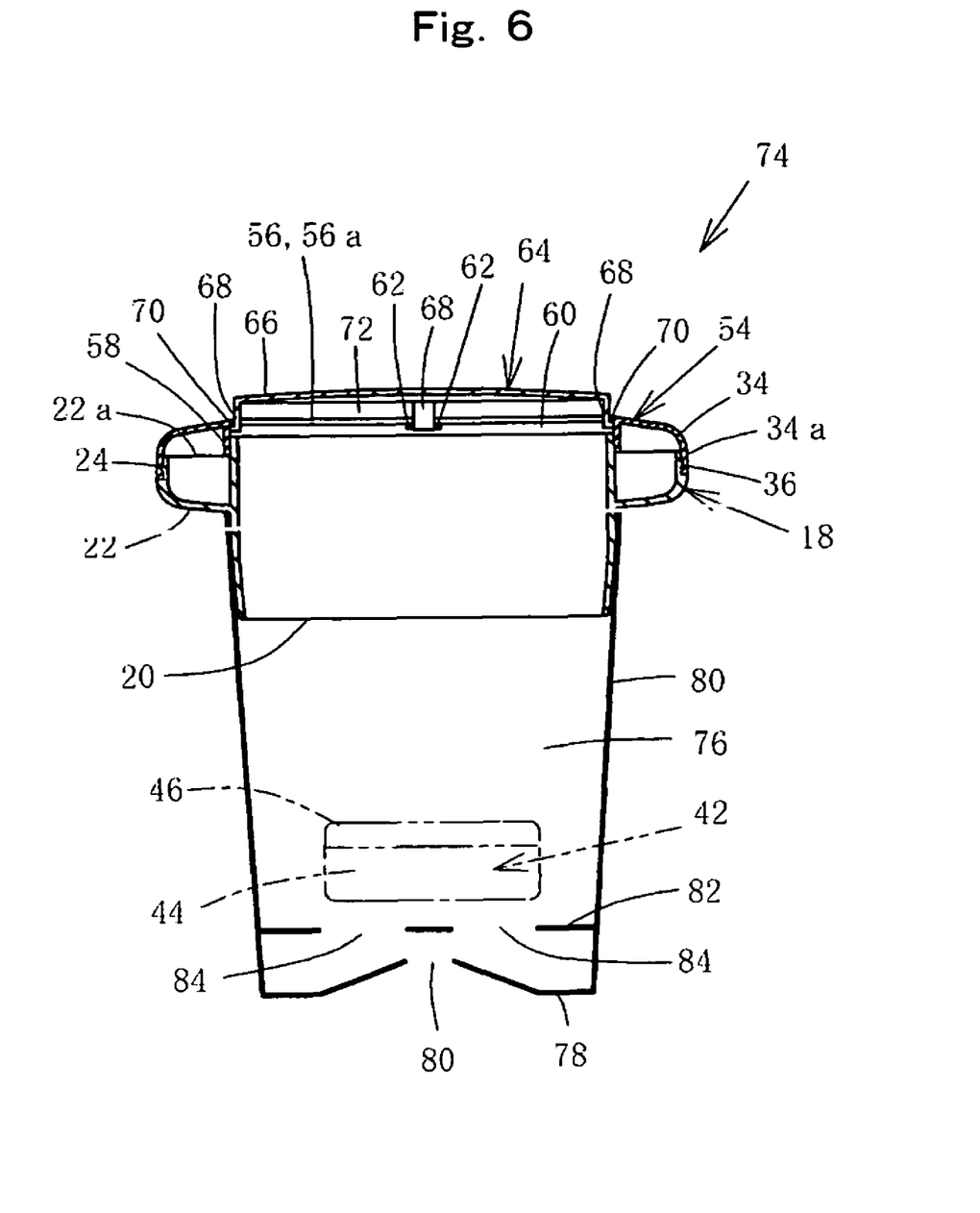
FIG. 6 is a longitudinal sectional view of a bubbling bath additive container according to a third embodiment of this invention.

Next, a third embodiment of this invention will be described with reference to FIG. 6. Here, the same members as in the above embodiments are denoted by the same numerals and will not be described further in detail. A bubbling bath additive container 74 of this embodiment is provided with a cup-like housing member 76 in which the bubbling bath additive 42 is to be put. The housing member 76 is made of a thin synthetic resin and has an appropriate shape-holding property. It is provided a circular bottom part 78 and a cylindrical lateral part 80. An upper end part of the lateral part 80 is attached by being fitted or adhered to a part near a lower end part on the outer surface of the cylindrical part 20 of the lower case 18. In the bottom part 78, a slit of a predetermined shape is formed and the inner part of the slit is bent toward the inside of the bottom part 78, thus opening a suction port 80. On the inner side of the cup member 76, an inner bottom part 82 is provided near the bottom part 78 and parallel to the bottom part 78. A permeating hole 84 is provided in the inner bottom part 82. The shapes of the suction port 80 of the bottom part 78 and the permeating hole 84 of the inner bottom part 82 can be freely designed. Also, the container can be used without having the inner bottom part 82.

Next, the way of using the bubbling bath additive container 74 of this embodiment will be described. First, the upper case 54 is attached to the lower case 18, and the bubbling bath additive 42 is put into the housing member 76. The supporting part 68 of the lid member 64 is elastically deformed and inserted to the lower side of the circumferential edge part 56a of the aperture 56 of the upper case 54, and the lid member is retained to the upper case 54. The bubbling bath additive 42 is set on the inner bottom part 82 of the housing member 76. In this state, the bubbling bath additive container 74 together with the bubbling bath additive 42 is put into bath water in a bathtub.

Then, bath water enters from the permeating hole 84 of the inner bottom part 82 through the suction port 80 of the cup member 76, and bubbles generated by the bubbling bath additive 42 are ejected from the ejection port 72. The repulsive force of the ejected bubbles causes the bubbling bath additive container 74 to rotate, and the bubbles spread the surface of the bath water and fill the bathtub.

The bubbling bath additive container 74 of this embodiment has the same effects as the foregoing embodiments. The cup member 76 is durable and can be used repeatedly. If it is made of a transparent resin, the state of dissolution of the bubbling bath additive 42 can be confirmed from outside. Also, the suction port 80 may be closed by a net.

Figure 7:
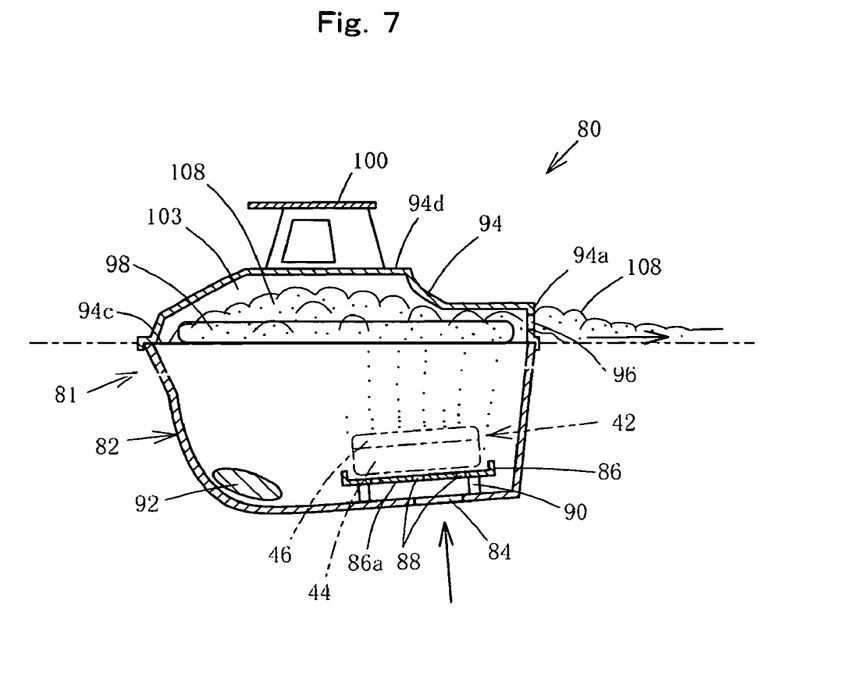
FIG. 7 is a longitudinal sectional view of a bubbling bath additive container according to a fourth embodiment of this invention.
Figure 8:
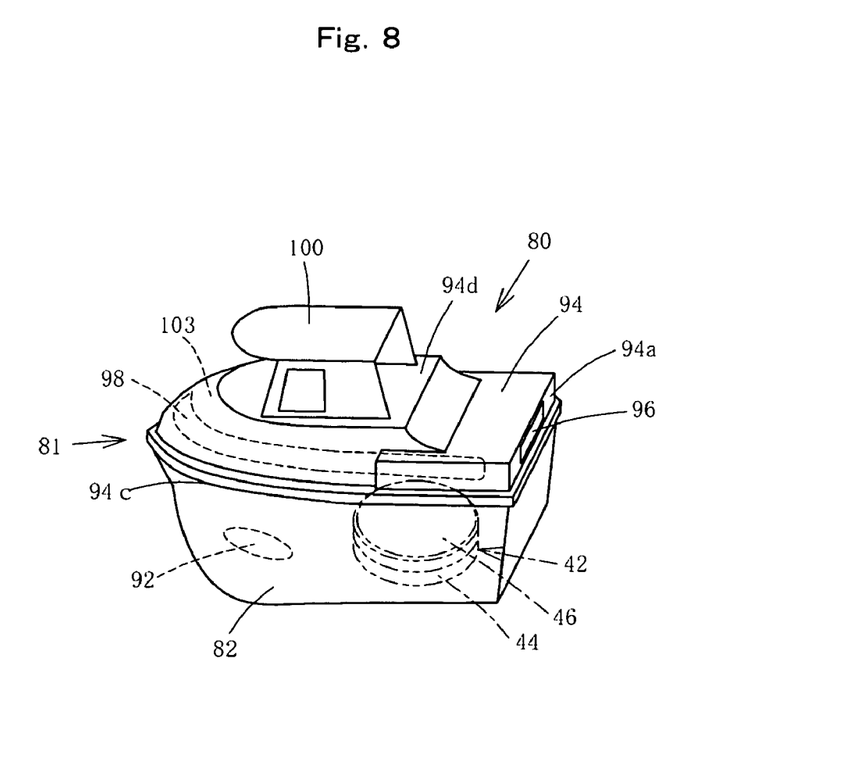
FIG. 8 is a perspective view of the bubbling bath additive container according to the fourth embodiment of this invention.

Next, a fourth embodiment of this invention will be described with reference to FIG. 7 and FIG. 8. Here, the same members as in the above embodiments are denoted by the same numerals and will not be described further in detail. A bubbling bath additive container 80 of this embodiment relates to a bath additive toy and includes a body 81 formed in the shape of a ship. Its lower part is a lower body part 82 including the bottom of the ship. In the lower body part 82, a suction port 84 through which water enters is formed at a position slightly rearward in the bottom part. Inside the suction port 84, a holding member 86 is provided in which the bath additive 42, later described, is to be put. The holding member 86 has a circular plate-shape and plural permeating holes 88 are provided in a bottom part 86a of the plate-shape. The bottom part 86a is fixed to the inner bottom part of the lower body part 82 via a leg part 90 so that the bottom part 86a faces and covers the suction port 84. A weight 92 having a proper weight is attached to a forward part of the bottom part of the lower body part 82.

The upper part of the bubbling bath additive container 80 is an upper body part 94 formed in the shape of an upper part of a ship. The upper body part 94 is attached to the lower body part 82 by a retaining member, not shown, substantially without having any spacing between them. The inner side of the upper body part 94 is a bubble housing space 103 in which bubbles 108 generated by the bath additive 42 are accumulated. In a rear side face 94a of the upper body part 94, an ejection port 96 through which the fully accumulated bubbles 108 are ejected is provided, penetrating the inside to the outside.

On the inner side of a side face 94b of the forward part and both lateral edge parts except for the side face 94a of the upper body part 94, a floating member 98 of expanded polystyrene or the like is attached along a lower edge part 94c of the upper body part 94. On a flatly formed top side 94d of the upper body part 94, an ornament 100 in the shape of a roof part of a ship is mounted.

In the holding member 86 of the lower body part 82 of the bubbling bath additive container 80, the solid bubbling bath additive 42 containing bath additive ingredients is put. The bubbling bath additive 42 has a two-layer or two-unit structure, including a layer of the bubbling agent 44 containing a carbon dioxide generating element and the surfactant 46 containing a soap element, detergent element and other bath additive ingredients. The surfactant 46 is formed to be thinner than the bubbling agent 44. As the bath additive ingredients contained in the bubbling bath additive 42, various hot spring elements can be selected appropriately.

Next, the way of using the bubbling bath additive container 80 of this embodiment will be described. First, the upper body part 94 is opened from the lower body part 82, then the bubbling bath additive 42 is set into the holding member 86 of the lower body part 82, and the upper body part 94 is closed to the lower body part 82. At this point, engagement parts, not shown, retain each other. In this state, the bubbling bath additive container 80 together with the bubbling bath additive 42 is put into bath water in a bathtub.

Bath water enters the bubbling bath additive container 80 from the suction port 84 of the lower body part 82. However, the floating member 98 causes the upper body part 94 to be situated above the water surface, and the lower body part 82 is situated below the water surface. Bath water enters from the suction port 84 of the lower body part 82 and dissolves the bubbling agent 44 and the surfactant 46 of the bubbling bath additive 42. The generated carbon dioxide strikes and stirs the dissolved surfactant 46, thus forming bubbles. Since water passes through the permeating hole 88 of the holing member 86, the water evenly contacts around the bubbling bath additive 42 and efficiently forms bubbles. Then, these bubbles rise, fill the bubble housing space 103 in the upper body part 94 as the bubbles 108, and are ejected outward from the ejection port 96. In this case, the bubble housing space 103 is a space where the bubbles 108 formed by the surfactant and air bubbles are accumulated, and the bubbles can be ejected continuously from the ejection port 96. The bubbles 108 are ejected rearward of the bubbling bath additive container 80 from the ejection port 96, and the repulsive force of the ejected bubbles 108 causes the bubbling bath additive container 80 to move forward. The bubbles 108 automatically spread on the surface of the bath water and form a layer of the even and fine bubbles 108, filling the bathtub.

With the bubbling bath additive container 80 of this embodiment, bubbles of the surfactant 46 can be easily formed and the layer of the fine bubbles 108 can be formed on the bath water surface in the bathtub. When bathing, one can feel the tough of the bubbles 108 and comfortably wash the body. Also, since the bubbling bath additive container 80 moves forward on the water surface by ejecting the bubbles 108, its movement is fun. Since the bubbles 108 remain on the traces, this also interests the user and the bubbles 108 can be spread on the water surface efficiently. Since the bubbling bath additive 42 is divided into the two layers of the bubbling agent 44 and the surfactant 46, the bubbling is good. Also, since the bubble housing space 103 is provided in the upper body part 94, the bubbles 108 will not be crushed and the even bubbles 108 are accumulated. As the bubbles are ejected, the even and beautiful bubbles 108 can be spread in the bath water.

Moreover, as the weight 92 and the floating member 98 are provided in the bubbling bath additive container 80, the waterline can be set to be situated at a proper position by adjusting the weight and buoyancy. Thus, adjustment can be made so that the bubble housing space 103 will be situated above the water surface while the bubbling bath additive 42 will be situated below the water surface, and bubbles can be generated securely and continuously until the bath additive is completely dissolved.

The bubbling bath additive container of this invention is not limited to the above embodiments, and other than a floating container, it may be a bubbling bath additive container fixed to a wall of a bathtub with a suction cup or the like when it is used. Also in this case, fine bubbles can be spread on the water surface by a surfactant and a bubbling agent. Moreover, their size, number of units, material, shape, and relative layout thereof can be appropriately changed. For example, the surfactant may be a bathtub detergent. By putting this bubbling bath additive into the hot water and causing it to bubble before draining the hot water after bathing so that bubbles of the bathtub detergent float on the water surface, and then draining the hot water, the stain on the inner wall of the bathtub is automatically flushed away with the bubbles of the bathtub detergent.

Also, the bubbling bath additive put into the bubbling bath additive container may be different from the bubbling bath additive that is the bath additive having the two-layer structure. As the surfactant element contained in the bubbling bath additive, a synthetic detergent or the like can be selected appropriately.

The invention claimed is:

1. A bubbling bath additive container having a housing member that houses a bubbling bath additive made of a surfactant and a bubbling agent, a floating part that is situated above this housing member and floats on a water surface, at least one ejection port that is provided above a waterline of the floating part and through which bubbles formed by the bubbling bath additive are ejected outward from inside, and a suction port that is formed near a lower end part of the housing member and through which water flows inward from outside, and characterized in that on an upper surface of the floating part, a recessed part provided radially toward a circumferential edge part is arranged next to the at least one ejection port.

2. The bubbling bath additive container as claimed in claim 1, characterized in that the floating part is formed substantially in a circle, the at least one ejection port is provided concentrically with the upper surface of the floating part, and a plurality of the ejection ports is provided at substantially equal intervals along a circumferential direction of the floating part.

3. The bubbling bath additive container as claimed in claim 1, characterized in that the bubbling bath additive is situated above the suction port of the housing member.

4. A bubbling bath additive container having a housing member that houses a bubbling bath additive made of a surfactant and a bubbling agent, a floatinq part that is situated above this housing member and floats on a water surface, an ejection port that is provided above a waterline of the floating part and through which bubbles formed by the bubbling bath additive are ejected outward from inside, and a suction port that is formed near a lower end part of the housing member and through which water flows inward from outside, and characterized in that the housing member is provided with an inner bottom part having a permeating hole between the suction port and the floating part, and the bubbling bath additive is situated in the inner bottom part.

5. The bubbling bath additive container as claimed in claim 4, characterized in that the floating part is formed substantially in a circle, the ejection port is provided concentrically with an upper surface of the floating part, and a plurality of the ejection ports is provided at substantially equal intervals along a circumferential direction of the floating part.

6. A bubbling bath additive container having a hollow body floating on a water surface with a part thereof situated below a waterline, the body having a lower body part that is situated below the water surface and houses therein a bubbling bath additive including a surfactant and a bubbling agent, a suction port that is provided in the lower body part and through which water flows inward from outside, an upper body part that is situated above the water surface, is mounted to the lower body part and forms a bubble housing space with its inside filled with bubbles formed by the bubbling bath additive, and an ejection port that is provided above and near the waterline and through which the bubbles filling the bubble housing space are ejected outward from inside, and characterized in that the body is provided with a weight that adjusts the position of the body relative to the water surface, and it is adjusted that the bubbling bath additive is situated below the water surface.

7. The bubbling bath additive container as claimed in claim 6, characterized in that the body is provided with a floating member that adjusts the position of the body relative to the water surface, and it is adjusted so that the bubble housing space is situated above the water surface.

8. A bubbling bath additive container having a hollow body floating on a water surface with a art thereof situated below a waterline the body having a lower body part that is situated below the water surface and houses therein a bubbling bath additive including a surfactant and a bubbling agent, a suction port that is provided in the lower body part and through which water flows inward from outside, an upper body part that is situated above the water surface, is mounted to the lower body part and forms a bubble housing space with its inside filled with bubbles formed by the bubbling bath additive, and an ejection port that is provided above and near the waterline and through which the bubbles filling the bubble housing space are ejected outward from inside, wherein the suction port is provided in a bottom part of the body, and inside the suction port, a holding member that holds the bath additive is fixed to the lower body part, and wherein the holding member is shaped to be situated to cover the suction port, and a permeating hole through which water flows is formed in the holding member.

9. The bubbling bath additive container as claimed in claim 8, characterized in that the, body is provided with a floating member that adjusts the position of the body relative to the water surface, and it is adjusted so that the bubble housing space is situated above the water surface.

\* \* \* \* \*